(12) United States Patent
Vinti

(10) Patent No.: US 12,014,421 B2
(45) Date of Patent: Jun. 18, 2024

(54) SYSTEM FOR PROMOTING HEALTH EQUITY IN DIVERSE AND UNDERSERVED GROUPS THROUGH MULTIFACETED FINANCIAL INVESTMENT DESIGN EMPLOYING ARTIFICIAL INTELLIGENCE

(71) Applicant: Dante A. Vinti, Port Washington, NY (US)

(72) Inventor: Dante A. Vinti, Port Washington, NY (US)

( * ) Notice: Subject to any disclaimer, the term of this patent is extended or adjusted under 35 U.S.C. 154(b) by 0 days.

(21) Appl. No.: 18/507,247

(22) Filed: Nov. 13, 2023

(65) Prior Publication Data
US 2024/0095834 A1    Mar. 21, 2024

(51) Int. Cl.
*G06Q 40/06*    (2012.01)
*G16H 50/70*    (2018.01)

(52) U.S. Cl.
CPC ............. *G06Q 40/06* (2013.01); *G16H 50/70* (2018.01)

(58) Field of Classification Search
CPC ..... G06Q 40/06; G16H 50/70; G06F 21/6254
See application file for complete search history.

(56) References Cited

U.S. PATENT DOCUMENTS

| | | | |
|---|---|---|---|
| 2009/0046096 A1* | 2/2009 | Rampersad | G16H 40/63 345/419 |
| 2009/0150362 A1* | 6/2009 | Evenhaim | G06F 21/6254 |
| 2009/0204528 A1* | 8/2009 | Moses | G06Q 40/00 705/35 |
| 2010/0131423 A1* | 5/2010 | Meyer | G06Q 40/06 705/36 R |
| 2011/0185505 A1* | 8/2011 | Davis | A61M 16/0605 5/636 |
| 2012/0166218 A1* | 6/2012 | Reiner | G06Q 30/0278 705/2 |

* cited by examiner

*Primary Examiner* — Jay M. Patel

(57) ABSTRACT

The present invention provides a system for promoting health equity in diverse and underserved groups. It targets equity-affected diseases where disadvantaged groups face disproportionate clinical outcomes, such as, for example, peanut and tree nut food allergies, hypertension, diabetes, maternal mortality and sepsis, and adjusts for biases and inequity disease-causing factors using artificial intelligence systems. Multifaceted financial systems, investor segmentation, and health data profiling facilitate strategic investments. The system of this invention promotes ongoing monitoring, evaluation, and subsequent investment outreach to a health equity funding pool, fostering comprehensive health equity initiatives for diverse and underserved groups while prioritizing data security.

12 Claims, 5 Drawing Sheets

SYSTEM FOR PROMOTING HEALTH EQUITY IN DIVERSE AND UNDERSERVED GROUPS THROUGH MULTIFACETED FINANCIAL INVESTMENT DESIGN EMPLOYING ARTIFICIAL INTELLIGENCE

FIELD OF THE INVENTION

The present invention relates to the field of healthcare equity and, more specifically, to the use of artificial intelligence to improve healthcare equity among underserved and diverse groups through multifaceted financial investment systems.

BACKGROUND

Despite increased financial investments in healthcare in recent years, disparities in healthcare access and outcomes still exist, with the most pronounced inequities attributable to race, ethnicity, cultural background, and socioeconomic status. This inequitable distribution of healthcare resources results in a decrease in overall health and well-being of diverse and underserved populations. The present invention relates to a system designed to promote health equity, particularly in diverse and underserved groups, through a system that coordinates and facilitates the application of multifaceted financial investments to address health inequities. The system described herein employs advanced data mining, artificial intelligence, and unconventional financial techniques to identify, address, and rectify these disparities, ultimately aiming to improve healthcare outcomes and reduce inequities in the provision of clinical treatments.

Diverse and underserved groups are statistically more likely to suffer from a wide range of chronic and acute diseases, disabilities and other health conditions, including food allergies, cardiovascular disease, stroke, diabetes, kidney disease, cancer, and chronic lower respiratory disease. These diseases are some of the leading causes of death and disability in the United States. See, e.g., *Leading Causes of Death*. U.S. Centers for Disease Control and Prevention, 2020. One contributing factor to such inequity is the underrepresentation or exclusion of diverse and underserved individuals in pharmaceutical, biotechnology and medical device clinical trials. This exclusion creates challenges in identifying the applicability, safety, and effectiveness of treatments for certain demographic groups. This issue holds particular importance in the context of technologies designed to alleviate conditions that significantly impact diverse and underserved communities.

As an example, peanut and tree nut allergies are two of the most common food allergies in the United States. Indeed, food allergies, particularly those that significantly impact major life activities such as breathing, eating, and other physiological functions, are disabilities under Section 504 of the Rehabilitation Act of 1973, a federal law in the United States. While these disabilities can impact people of all backgrounds, there is growing evidence that diverse and underserved groups face unique challenges and disparities in managing and coping with peanut and tree nut allergies. These disparities disproportionately affect underserved and marginalized populations, including individuals from racial and ethnic minorities, low-income communities, and those with limited access to healthcare resources. The problems associated with peanut and tree nut allergies in diverse and underserved groups include health inequity-related factors such as delayed diagnosis and lack of early awareness, limited access to healthcare and allergists which can result in missed opportunities for early detection and appropriate management, limited access to affordable allergen-free foods, cultural and language barriers which hinder effective communication between patients and healthcare providers and lead to misunderstandings about allergy management, dietary restrictions, and emergency response procedures, with underserved communities often experiencing disparities in accessing timely and effective emergency care in the event of severe allergic reactions which can result in adverse health outcomes and, in some cases, fatalities. Further, living with peanut and tree nut allergies can have a profound negative psychosocial impact on individuals and their families, including increased stress, anxiety, and social isolation which are magnified in communities where support systems are limited. For example, one recent survey study of 51,819 households found that Black, Asian and Hispanic individuals were more likely to report having food allergies. In addition, the prevalence of food allergies was lowest among households in the highest income bracket. See Jiang, J., Warren, C. M., Brewer, A., Soffer, G., & Gupta, R. S. (2023), *Racial, Ethnic, and Socioeconomic Differences in Food Allergies in the US*, JAMA Netw Open. 2023.

Disparities in access to epinephrine auto-injectors are another unfortunate reality when it comes to health inequities, with significant differences observed between racial and ethnic groups. Numerous studies and healthcare data have pointed to a troubling trend where epinephrine auto-injectors, crucial for the management of severe allergic reactions, are not as readily available to Black children. See, e.g., Cohen, J. S., Agbim, C., Hrdy, M., Mottla, M. E., Goyal, M. K., & Breslin, K., *Epinephrine Autoinjector Prescription Filling After Pediatric Emergency Department Discharge*, Allergy Asthma Proc., 2021. This disparity can be attributed to a complex interplay of factors, including limited access to quality healthcare, insurance coverage, socioeconomic barriers, and geographical variations in healthcare infrastructure. Such discrepancies in access to life-saving tools like epinephrine auto-injectors only serve to exacerbate health inequities, emphasizing the urgent need for comprehensive efforts such as the present invention to address these disparities and ensure that individuals of all races and backgrounds have equitable access to essential medical resources.

Studies have also demonstrated a potential link between living in ZIP codes characterized as food deserts and the occurrence of food allergies. Food deserts are areas characterized by limited or inadequate access to affordable, nutritious, and fresh food options, such as fruits and vegetables. These regions are often devoid of grocery stores, and residents often rely heavily on convenience stores or fast-food outlets for their daily sustenance. Food deserts have a particularly pronounced impact on diverse and underserved communities, exacerbating disparities in health and nutrition. When it comes to food allergies, these communities are especially vulnerable. The lack of access to a variety of wholesome foods makes it challenging for individuals to maintain a balanced diet, which is crucial for managing food allergies. The overreliance on processed and less nutritious options in food deserts can increase the risk of food allergies or allergic reactions, making it a pressing concern for those already facing limited resources and healthcare access. Addressing food deserts is not only a matter of food security, but also a critical step in mitigating health inequalities, particularly regarding conditions like food allergies.

Compounding these disparities is that clinical trials for treatments, such as for peanut and tree nut allergies, often do not adequately include minority groups, which can result in significant disparities in research, diagnosis, treatment, and outcomes. Lack of diversity in trial participants is a key contributor to health inequities in the prevention and treatment of severe food allergies. Clinical trials typically struggle to recruit a diverse pool of participants, which can lead to a lack of representation from minority populations. This underrepresentation can make it challenging to understand how peanut and tree nut allergies and treatments for those disabilities affect different racial and ethnic groups. Results of clinical trials lacking in minority representation are not easily generalizable to minority groups, potentially leading to misinformed or less effective treatment strategies for these populations.

Another example of an equity-affected disease is COVID-19. The COVID-19 pandemic had a disproportionate negative impact on various diverse groups in society, highlighting existing health and socioeconomic disparities. These disparities were driven by a combination of pre-existing inequalities and differential access to resources and healthcare. Black, Hispanic, and Indigenous communities in many countries experienced higher rates of COVID-19 infection often due to factors like living in crowded areas, working in essential jobs, and limited access to healthcare. These communities also saw higher mortality rates due to underlying health disparities, lack of access to quality healthcare, and a higher prevalence of pre-existing conditions, such as diabetes and hypertension, which increase the severity of COVID-19. Limited access to quality healthcare and testing facilities further exacerbated these disparities, especially during the early onset of COVID-19.

Sepsis is another equity-affected disease that disproportionately affects diverse and underserved individuals. For example, a retrospective analysis presented at the 2023 AAP National Conference & Exhibition revealed significant racial disparities in pediatric sepsis mortality. The study, titled "*Racial Disparity in Pediatric Sepsis Mortality*," examined pediatric sepsis deaths between January 2018 and April 2022 at the Arkansas Childrens Hospital (ACH). Findings indicated that Black children at ACH were 2.5 times more likely to succumb to sepsis, with a mortality rate of 3.13% in Black children compared to 1.27% in White children. Despite advancements in early recognition and treatment of sepsis using automated detection tools, sepsis-related mortality in Black children persists at a higher rate. The study highlights the need for further investigations into potential biases, socioeconomic factors, and genetic predispositions leading to these racial disparities in pediatric sepsis outcomes.

Disparities in the maternal mortality rate also persist as a pressing and alarming concern in the United States. Statistics reveal a stark contrast between the mortality rates of Black, Indigenous, and other women of color. According to various studies, these women are two to three times more likely to die from pregnancy-related complications. This discrepancy transcends income and education levels, indicating a systemic issue deeply rooted within the healthcare system. Factors such as inadequate access to quality healthcare, implicit biases among healthcare providers, and the effects of chronic stress due to societal inequalities contribute significantly to these disparities. The urgency to address and rectify these inequities in maternal healthcare remains a critical challenge for the nation's health system.

Artificial Intelligence or AI, which harnesses significantly augmented computational capabilities to acquire knowledge and execute tasks typically within the human domain, is rapidly becoming a pivotal catalyst for advancements in the healthcare industry. The potential of AI has become unmistakably clear in various mission-critical domains such as drug discovery, understanding disease causes, managing clinical trials, and optimizing the manufacturing supply chain. In the realm of addressing health inequities, it is imperative to review the strides made by the industry in integrating AI and Machine Learning (ML) capabilities within the healthcare sector, emphasizing their pivotal role. Additionally, it is crucial to identify and surmount the key internal and external barriers that impede the effective utilization of AI in combatting health disparities. This involves engaging with institutions investing in healthcare, patients, and healthcare providers to ensure that AI/ML initiatives are shaped by a diverse array of perspectives, promoting inclusivity and relevance in the context of health equity efforts. The invention described herein strives to reduce health disparities through the use of AI advancements in a complex architecture specifically aimed at addressing health inequities. While the use of AI alone is insufficient to address health inequities, its use as one component in the system of the present invention is valuable to eliminate health inequities. With the influx of new AI products in conjunction with venture capital and other sources of private and public funding, the ability to detect the root causes of health inequities for a particular disease and project health outcomes in divers and underserved groups when those root causes are addressed is exponential.

The invention described herein addresses these critical issues by providing a comprehensive solution designed to improve the management and outcomes of disease, with a specific focus on reducing disparities in diverse and underserved groups. Through the use of artificial intelligence and innovative technologies described herein, this system aims to better coordinate and facilitate the application of financial investments in treating such equity-affected diseases. This will enhance health equity in underserved and diverse groups and promote equity in healthcare outcomes.

DESCRIPTION OF THE RELATED ART

Health disparities have been a persistent challenge in healthcare systems worldwide. While advancements in medical science have led to the development of numerous treatments and interventions, access to these innovations has not been distributed evenly across different demographic groups. Diverse and underserved populations, including those characterized by race, gender, and socio-economic factors, often face substantial barriers in accessing quality healthcare and obtaining equitable clinical treatments. These disparities result in adverse health outcomes, reduced life expectancy, and increased healthcare costs for both affected individuals and society at large.

A number of transformative organizations have made strides in advancing health equity. For example, Hip Hop Public Health, founded by the pioneering and multi-talented Dr. Olajide Williams, is an innovative initiative that harnesses the power of hip hop music to address health equity and promote wellness in underserved communities. Dr. Williams, a neurologist and professor, recognized the need for culturally relevant health education tools to reach diverse populations. Hip Hop Public Health, as run by the accomplished and savvy CEO Lori Rose Benson, utilizes the universal appeal of hip hop music and its influence on youth culture to deliver vital health messages in an engaging and accessible manner. Through catchy songs, music videos, and interactive content, Hip Hop Public Health tackles various health topics, from chronic disease prevention to mental health awareness. Dr. Williams' approach through Hip Hop Public Health aims to bridge the gap in health education and access for underserved communities, especially among young people. Hip Hop Public Health's efforts help drive behavioral change, encourage healthier lifestyle choices and promote health equity.

Another example is the collection of medical schools across the United States who have dedicated efforts to promote health equity in their educational programs and initiatives. These medical institutions prioritize training future healthcare professionals to understand and address disparities in healthcare. They integrate health equity principles into their curriculum, focusing on social determinants of health, cultural competence, and the challenges faced by underserved populations in healthcare. Many medical schools have established centers, programs, and initiatives aimed at advancing health equity through education, research, and advocacy. Students are often encouraged to engage in community outreach and service learning opportunities, gaining hands-on experience in serving underprivileged and marginalized communities. These schools also conduct research, participating in studies addressing various aspects of health equity, such as the impact of socioeconomic factors on health outcomes and interventions to reduce disparities in healthcare access. Their commitment involves multidisciplinary approaches, collaborating with different departments, community organizations, and policy initiatives to address systemic issues affecting underserved communities.

Another notable example is the Catholic Health Association (CHA) in the United States. The CHA represents hundreds of hospitals and healthcare facilities that often operate in underserved and marginalized communities, emphasizing the provision of healthcare services regardless of patients' ability to pay. The CHA organizations are known for their commitment to providing care to the most vulnerable populations. They often offer financial assistance, community outreach programs, and various support services, particularly focusing on those without adequate access to healthcare. These institutions typically prioritize not only treating the ill but also addressing social determinants of health, striving to improve overall community wellness. Furthermore, these facilities embrace the Catholic (e.g., Augustinian, Dominican, Franciscan, Jesuit, Marianist) social teachings, which advocate for truth, unity, love, social justice and the dignity of every person. This ethos often drives their initiatives aimed at health equity, emphasizing compassionate care for all, regardless of socioeconomic status or background.

Another example of an institution that tackles health inequities is the Robert Wood Johnson Foundation (RWJF), a foundation established by Johnson & Johnson. It is one of the largest philanthropies in the United States dedicated solely to health. RWJF focuses on advancing health equity by addressing social determinants of health and promoting policies and initiatives to improve health outcomes for marginalized populations. The foundation supports research, innovative projects, and advocacy efforts that aim to reduce health disparities and create a culture of health for all, including through its "Culture of Health" approach, which emphasizes that health is influenced by a multitude of factors beyond medical care, such as education, environment, housing, and socioeconomic status.

The Health Resources and Services Administration (HRSA), an agency of the U.S. Department of Health and Human Services, also focuses on improving access to healthcare services for people who are uninsured, isolated, or medically vulnerable. HRSA operates several programs and initiatives aimed at promoting health equity and reducing disparities in healthcare. One prominent initiative is the Health Center Program, which supports a network of community-based health centers that provide comprehensive and affordable primary care services to underserved populations, including those in rural or inner-city areas. HRSA's efforts involve grant programs, workforce development initiatives, and collaborations with state and local organizations to improve health outcomes and reduce disparities among underserved populations across the United States.

Other conventional efforts to address health disparities have traditionally had less of a focus on utilizing emerging technologies, and have instead focused on policy and awareness initiatives, which, while important, have not consistently yielded significant improvements in closing the healthcare equity gap. The development of more effective strategies for promoting health equity is, therefore, an ongoing and critical challenge in the field of healthcare.

SUMMARY OF THE INVENTION

The system disclosed herein represents a novel and innovative approach to addressing health disparities by coordinating, focusing and facilitating the application of financial investments as a means to drive positive change in healthcare outcomes. This invention combines cutting-edge technologies, including data mining, artificial intelligence, and unconventional financial systems, to identify, evaluate, and mitigate disparities in the clinical treatment of diseases affecting diverse and underserved groups.

The invention comprises several interrelated components, including data collection and analysis tools, a clinical decisions processing system that utilizes artificial intelligence to identify one or more inequity disease-causing factors contributing to disproportionate clinical outcomes among diverse and underserved groups, and an ethical artificial assessment platform designed to identify biases in the clinical treatment of equity-affected diseases and determine disparities caused by these biases.

Additionally, the system features an equity-focused investment coordination module with two tiers. The first tier directs financial investments to a select group of investors who have demonstrated prior commitments to addressing equity-affected diseases. If these initial investments do not yield the desired outcomes, the system activates a selected and targeted second tier, involving a larger group or pool, such as government entities, to channel financial resources toward the identified health equity goals.

These components work together to identify diseases where diverse and underserved groups are disproportionately disadvantaged, pinpoint the factors contributing to these disparities, and forecast potential financial returns from addressing them. Through targeted investments in clinical treatments that specifically target the identified inequities and biases, the system seeks to bring about positive change in healthcare outcomes for these populations.

Investment from private investors such as private equity firms have the potential to reduce disparities in health by supporting and funding drug development initiatives for diverse and underserved groups. The healthcare industry continually faces the challenge of financial forecasting, particularly when it pertains to the treatment of equity-affected diseases that disproportionately affect specific diverse or underserved populations. For example, there are generally two primary avenues for financing the crucial later stages of drug development and commercialization: partnering with a major pharmaceutical company or conducting an initial public offering (IPO). Regrettably, these avenues often overlook diseases and conditions that disproportionately affect diverse and underserved communities. As an expanding array of private investors such as private equity firms are entering the field of drug development, driven by the desire to exploit the increasing disparity between the available funding for clinical research and the mounting competition among drugs vying for those funds, the opportunity exists for investment in diseases that disproportionately affect diverse and underserved groups. It is therefore imperative to improve the application of financial investments to address inequity disease-causing factors. The present invention is aimed at doing that. Through accurate financial forecasting—an imperative for investors, pharmaceutical companies, healthcare organizations, insurers, and policymakers—and the use of AI as described herein, financial investment targeting diseases affecting diverse and underserved groups can be increased. While the presence of clinical biases and inequity disease-causing factors in healthcare data often hinders the accuracy of these forecasts, the innovation described provides an advanced financial forecasting platform that corrects for and negates these biases. This provides more reliable insights into the financial implications of clinical treatment for such groups and thus investment.

In summary, the system for promoting health equity described in this patent application represents a groundbreaking approach to addressing disparities in clinical treatment among diverse and underserved groups. By harnessing the power of data-driven decision-making, artificial intelligence, and strategic financial investments, the invention not only improves healthcare outcomes but also contributes to a more equitable healthcare system that benefits all members of society.

Accordingly, in one aspect, the invention features system for promoting health equity in diverse and underserved groups through select and tangible components and methods. The system includes a data mining processor for scanning health predominant sources to collect (i) disease data and (ii) clinical treatment options for said disease data. A disease data processor stores the disease data in a disease database and correlates the disease data with the clinical treatment options based on race, income, and socio-economic factors. An equity-affected disease identification processor identifies one or more equity-affected diseases from the disease database where diverse and underserved groups are disproportionately disadvantaged in the clinical treatment options compared to the general population. A clinical decisions processing system comprising artificial intelligence identifies one or more inequity disease-causing factors causing said diverse and underserved groups to suffer disproportionate clinical outcomes for the equity-affected diseases. An ethical artificial intelligence assessment processor then identifies one or more biases in the clinical treatment of such equity-affected diseases to determine disparities caused by the biases. An equity-affected disease adjustor processor adjusts clinical outcomes of the equity-affected diseases when correcting the biases and said inequity disease-causing factors, wherein the equity-affected disease adjustor processor includes artificial intelligence trained on at least three disciplines of science to correct said biases and inequity disease-causing factors. A financial forecasting processor employing a financial forecasting platform calculates potential future earnings and return-on-investment of clinical treatments of the equity-affected diseases when accounting for the biases and inequity disease-causing factors. An investor segmentation and profiling processor determines a predetermined first set of investors based on previous investments by the first set of investors in healthcare targeting diverse and underserved communities. A first transmittal module transmits the potential future earnings to the predetermined first set of investors to coordinate the application of a first financial investment in clinical treatments that target inequity-disease causing factors for the equity-affected diseases. A monitoring processor continuously monitors the change in the prevalence of equity-affected diseases after said first financial investment. An evaluation processor then determines the clinical effects of said the financial investment in the clinical treatments that target inequity-disease causing factors. A health segmentation data profiler processor identifies a health equity funding pool comprised of one or more investors that have not previously invested in health equity but who have shown a predisposition to invest in healthcare treatments to benefit diverse and underserved groups. A second transmittal module transmits to the health equity funding pool the potential future earnings and return-on-investment for equity-affected diseases that did not decrease after the first financial investment to further increase the potential for investment in equity-affected diseases.

DETAILED DESCRIPTION

Figure 1:
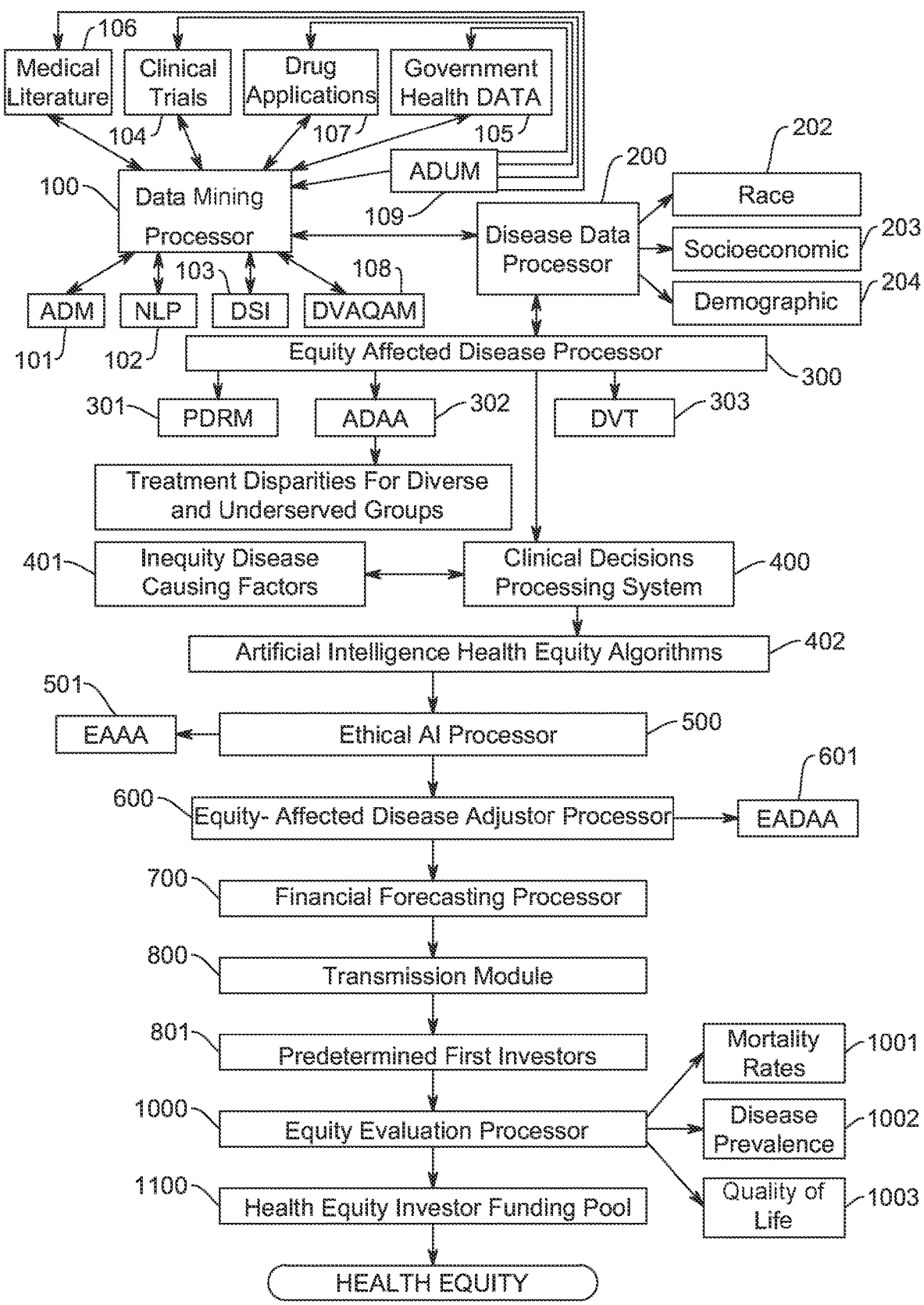
FIG. 1 is a diagrammatic overview of the system architecture of an exemplary embodiment of the present invention.

FIG. 1 is a diagrammatic overview of an artificial intelligence driven health equity system architecture intended to enhance financial investment for healthcare for diverse and underrepresent groups. The data mining processor 100 for health predominant sources presented herein addresses the aforementioned health equity challenges by offering an efficient solution for collecting disease data and clinical treatment options. The processor in this embodiment employs advanced data mining (ADM) 101 and natural language processing (NLP) 102 techniques to scan a variety of health predominant sources, including, but not limited to, clinical trials, drug applications, government health data, medical research papers, clinical notes, patient records, clinical guidelines, and electronic health records. In some embodiments, the data mining processor 100 utilizes ADM techniques such as data cleaning and preparation, tracking patterns, classification, association, outlier detection, clustering, regression, prediction, sequential patterns, decision trees, statistical techniques, visualization, neural networks, data warehousing, and/or long-term memory processing. In some embodiments, the data mining processor 100 utilizes ADM techniques such as sentiment analysis, named entity recognition, summarization, topic modeling, text classification, keyword extraction, and/or lemmatization and stemming.

The invention systematically identifies and extracts relevant information related to diseases, such as disease characteristics, symptoms, risk factors, prevalence, and epidemiological data. Furthermore, it collects clinical treatment options, encompassing various therapeutic approaches, medications, surgeries, and therapies associated with the respective diseases. The collected data is then structured, categorized, and stored in a database, providing a valuable resource for investors, researchers, and decision-makers. The data mining processor 100 comprises several supporting components. Data Source Identification (DSI) 103 enables the data mining processor 100 to identify and access health predominant sources of data, including but not limited to clinical trial databases 104, government health databases 105, medical literature databases 106, drug applications 107, electronic health records, clinical notes, patient records, and clinical guidelines. Access to these sources can be established through public sources, secure APIs, web scraping, or other appropriate methods.

The processor employs natural language processing algorithms 102 to extract text and relevant information from the selected sources. It identifies disease-related data and clinical treatment options within the text, including mentions of diseases, symptoms, risk factors, treatments, and clinical guidelines. Extracted data is organized and categorized according to predefined parameters, such as disease type, severity, treatment modalities, and patient outcomes. This structured information is then stored in a database for easy retrieval and analysis. To ensure the accuracy and reliability of collected information, the data mining processor 100 incorporates data validation and quality assurance mechanisms (DVAQAM) 108. These mechanisms can include cross-referencing data across multiple sources, checking for inconsistencies, and verifying against authoritative databases. The data mining processor 100 provides a user-friendly interface for accessing and querying the collected disease data and clinical treatment options. Users can search for specific diseases or treatments and retrieve relevant information.

The invention includes an automated data update mechanism (ADUM) 109 that periodically revisits data sources to maintain the most current and relevant information in the database. For example, ADUM 109 can be configured to revisit the data sources at periodic time intervals (e.g., once per hour, once per day, once per week, etc.). In some embodiments, ADUM 109 can revisit a data source after receiving an automated notification from the data source indicating that the data source includes new information.

The disease data processor 200 presented in this representative embodiment addresses the aforementioned challenges of health inequities in diverse and underserved populations by providing a comprehensive solution for storing disease data and correlating it with race 202, socioeconomics 203, demographics 204 and other factors, thereby enabling a more personalized approach to medical treatment, especially amongst diverse and underserved groups who have traditionally suffered from health inequities and disparities. The disease data processor 200 utilizes advanced data storage and correlation techniques to efficiently manage and analyze health data, race, socioeconomic, and demographic information. The disease data processor 200 systematically collects and stores disease data from various sources, including clinical trials 104, government health databases 105, medical literature 106, clinical notes, patient records, and clinical guidelines. In some embodiments, the disease data processor 200 receives the disease data from data mining processor 100. In some embodiments, disease data processor 200 has direct access to the data sources (not shown in FIG. 1).

Simultaneously with collecting disease data, the disease data processor 200 collects demographic data, such as race, gender, and socio-economic status, and correlates it with the disease data. This correlation is used to identify patterns and relationships between diseases and diverse and underserved groups that can inform health equity factors, medical decision-making, healthcare policy, medical research and financial investment in healthcare. Disease data and demographic information are systematically stored in a disease database. The disease database is designed to handle a wide range of data types, including structured and unstructured data, to ensure data integrity and accessibility. The disease data processor 200 employs advanced correlation algorithms to identify relationships between disease data and demographic factors. This includes analyzing how race, gender, and socio-economic status affect the prevalence of diseases, response to treatments, and overall patient outcomes in diverse and underserved populations. The disease data processor 200 includes measures for data analysis and reporting, allowing healthcare professionals, researchers, policymakers and investors to extract valuable insights from the correlated data. This analysis can inform treatment decisions, public health interventions, and medical research. The disease data processor 200 further incorporates robust data security measures to protect sensitive patient information and ensure compliance with HIPPA and data privacy regulations. A user-friendly interface allows users to query the disease database and access correlated disease data and demographic factors for research and decision-making.

The equity-affected disease identification processor 300 provided herein addresses the aforementioned challenges by offering a dedicated solution for recognizing diseases that disproportionately disadvantage diverse and underserved groups in clinical treatment options. The equity-affected disease identification processor 300 utilizes advanced data analysis and disease categorization techniques to efficiently identify and prioritize equity-affected diseases. The equity-affected disease identification processor 300 systematically scans the disease database for relevant data, analyzes the clinical treatment options, and compares treatment disparities among different demographic groups. The equity-affected disease identification processor 300 then categorizes diseases based on the magnitude of these disparities, highlighting those that significantly affect diverse and underserved populations. This information can be invaluable for financial investors, government agencies employing tax dollars to provide better health access, pharmaceutical companies, healthcare professionals, policymakers, and researchers in addressing health inequities. The equity-affected disease identification processor 300 comprises several key components. The processor data retriever module (PDRM) 301 retrieves disease data and clinical treatment options from the disease database, utilizing data collection and retrieval mechanisms. Advanced data analysis algorithm (ADAA) 302 is employed to assess treatment disparities among diverse and underserved groups for each disease in the database. Disparities can be quantified by comparing treatment outcomes, accessibility, and response rates. The equity-affected disease identification processor 300 categorizes diseases based on the level of disparity identified in clinical treatment options. Diseases that disproportionately disadvantage diverse and underserved groups are classified as equity-affected diseases. The equity-affected disease identification processor 300 may include data visualization tools (DVT) 303 to represent the identified equity-affected diseases, allowing for easy interpretation and decision-making by healthcare professionals, researchers, and policymakers. A user-friendly interface enables users to access the categorized equity-affected diseases, understand the treatment disparities, and make informed decisions based on the identified disparities.

The clinical decisions processing system 400 presented herein offers a dedicated solution for identifying inequity disease-causing factors 401 for equity-affected diseases. The clinical decisions processing system 400 utilizes advanced artificial intelligence techniques to analyze health data, demographics, and clinical outcomes, with the goal of identifying and quantifying the factors that disproportionately affect diverse and underserved groups in the context of specific diseases. The clinical decisions processing system 400 systematically collects and analyzes data, including disease data, demographic information, and clinical outcomes. Artificial intelligence health equity algorithms 402 are employed to identify patterns and correlations, ultimately pinpointing the specific inequity disease-causing factors. Advanced machine learning techniques, including supervised learning, unsupervised learning, and deep learning, are employed to analyze the integrated data. These algorithms uncover patterns and correlations within the data. The AI algorithms 402 systematically identify and quantify the disease-causing factors that contribute to disparities in specific diseases among diverse or underserved groups. These factors can include genetic predispositions, environmental exposures, lifestyle behaviors, healthcare access, and socio-economic determinants.

The ethical artificial intelligence assessment processor 500 presented herein offers a unique solution for identifying biases in clinical treatment practices for equity-affected diseases. The platform utilizes advanced machine learning and data analysis techniques, guided by ethical considerations, to examine healthcare data and clinical decision-making processes. The ethical artificial assessment processor 500 ensures that the AI system is trained on diverse and representative datasets that include a wide range of demographic groups. This helps the AI model learn from a variety of cases and reduces the risk of bias towards a particular group. Ethical artificial assessment processor 500 performs preprocessing techniques to the training data, such as data anonymization and de-identification, to remove any personally identifiable information (PII). This reduces the likelihood of the AI model learning or perpetuating biases. An ethical artificial assessment algorithm (EAAA) 501 performs bias detection and mitigation techniques to identify and address any existing biases in the AI model. This can involve adjusting the model's predictions to be more equitable and fairer across different demographic groups. The ethical artificial assessment algorithm 501 further conducts regular algorithmic fairness audits to evaluate the AI model's performance across different demographic groups. This involves examining the model's outcomes to identify and rectify disparities. EAAA 501 continuously monitors and improves AI models by retraining them with updated data and by addressing any biases or disparities that emerge over time.

"Hallucinations" in AI (aka AI misinformation), which involves the generation of inaccurate information presented as if it were correct, are also addressed. Addressing these AI hallucinations is vital for health equity as it helps mitigate biased decision-making and enhances the accuracy and fairness of AI-driven healthcare applications. The present invention also combats AI hallucinations through continuous medical education updating of the AI systems and verifying AI-generated data through peer-reviewed medical training materials and sources. Comprehensive and diverse datasets ensure AI systems generate more inclusive and accurate outputs, reducing the likelihood of hallucinations. In the system of the present invention, all known instances of hallucinations are promptly reported and corrected. Indeed, the present invention addresses ethical and safety concerns surrounding the use of artificial intelligence in healthcare. It establishes a platform for responsible AI in health and medicine by defining ethical standards, analyzing the scientific literature from experts in the field, and ensuing that AI advances in healthcare for diverse and underserved groups are aligned with patient needs.

The equity-affected disease adjustor processor 600 uses artificial intelligence to adjust existing clinical outcomes of the equity-affected diseases to account for biases and inequity causing factors and therefore predict outcomes of equity-affected diseases when biases and inequity causing outcomes are considered. Equity-affected disease adjustor algorithm (EADAA) 601 corrects biases and addresses factors contributing to health inequities in outcome prediction. The artificial intelligence of the equity-affected disease adjustor processor is trained on at least three disciplines of science to correct the biases and inequity disease-causing factors. The importance of training the artificial intelligence of the equity-affected disease adjustor processor across at least three disciplines cannot be overstated. Such multi-disciplinary training not only broadens the scope of knowledge but also enhances the adaptability and effectiveness of the AI system. By incorporating insights from various disciplines such as finance, biotechnology, and public health, the AI can better comprehend the intricate relationship between health disparities and inequities, societal factors, and economic impacts on disease outcomes. A multi-faceted approach enables the AI to discern a broader spectrum of variables, considering not only the medical aspects but also the social determinants and financial implications affecting disease outcomes in diverse communities. This holistic understanding is crucial for creating more equitable and effective disease adjustment models that cater to the complexities of various populations, ensuring fair and just outcomes in healthcare interventions.

Statistical and machine learning techniques as well as large language models are employed along with fairness-aware algorithms to remove, or at least neutralize, biases, especially biases towards diverse and underserved group. Biases in healthcare data, such as underrepresentation of certain demographics, can lead to misdiagnoses or inadequate treatment recommendations. When these biases are corrected, the predictive model can provide more accurate and tailored insights, improving patient care. Biased data may misguide resource allocation in healthcare, leading to overallocation to some groups and under allocation to diverse and underserved populations. Predictive models that account for inequity disease-causing factors and biases can provide more accurate risk assessments for various health conditions and the financial rewards in threated diseases that have largely been ignored in diverse and underserved communities. This allows healthcare providers to offer proactive preventive care to diverse and underserved individuals, reducing the overall disease burden and improving population health. In addition, correcting biases and inequity disease-causing factors will coordinate, focus and facilitate the application of financial investments for treatments and courses of action aimed at solving equity-affected diseases. These investments will lead to healthcare resources distributed more efficiently and equitably and benefit medical research and innovation.

Financial forecasting processor 700 calculates potential future earnings of clinical treatment of the equity-affected diseases when accounting for the clinical biases and inequity disease-causing factors. Financial forecasting processor 700 is designed to estimate potential future earnings in healthcare, specifically within the context of clinical treatment for equity-affected diseases. Financial forecasting processor 700 integrates healthcare data from multiple sources to project potential earnings based on anticipated treatment outcomes for diverse and underserved groups when the data is corrected, and biases removed. The Financial forecasting processor 700 utilizes fairness metrics to evaluate the accuracy and equity of the forecasts for different patient groups, ensuring that no demographic is disproportionately affected. The financial models provided by Financial forecasting processor 700 show investors that treating diverse and underserved populations can provide financial rewards by quantifying the potential benefits and financial implications of serving these groups. The model includes an analysis of the market size, growth potential, patient volume, reimbursement rates, tax incentives and costs associated with targeting investments in healthcare for diverse and underserved populations. It includes a comprehensive array of financial scenarios using an advanced algorithmic framework to formulate targeted investment recommendations. These recommendations serve a dual purpose: optimizing return on investment while strategically propelling the development of clinical solutions for equity-affected diseases within diverse and underserved communities. Operating on a data-intensive model, this system employs intricate predictive analytics that assess a wide spectrum of financial models and investment pathways, specifically focusing on initiatives addressing health disparities. This technical approach efficiently channels capital towards initiatives that not only yield financial gains but also contribute significantly to the amelioration of health disparities in marginalized communities affected by these specific diseases.

The investor segmentation and profiling processor (ISP) 727 utilizes a complex algorithmic methodology involving machine learning and data analytics to select investors based on their historical investment behavior. This process involves a multi-step technical approach. Initially, the ISP 727 aggregates and organizes vast amounts of historical investment data, encompassing details such as investment sectors, transaction volumes, asset classes, investment timelines, and associated risk profiles. This approach could entail mining unconventional textual data, such as social media posts, public forums, or even private investor correspondence. The system could use Natural Language Processing to analyze sentiment, language, and context within these sources, seeking indicators of investors' inclinations or sentiments toward particular sectors or thematic investments. By scraping and analyzing these unconventional data sources, the system would seek patterns in language or sentiment that suggest a positive or negative sentiment toward specific industries or investment themes. Uncovering phrases, sentiments, or language cues within these non-traditional data sources could provide unique insights into potential investor predispositions that might not be evident through traditional investment portfolios. Sentiment analysis on diverse textual data, could serve as a technical means to identify investors' leanings or interests that might not be explicitly reflected in their formal investment history but are embedded in their informal communications or online presence. Leveraging this data, the system applies sophisticated clustering algorithms and pattern recognition techniques to identify recurring investment patterns, sectorial preferences, and thematic inclinations of each investor. Through these techniques, the ISP 727 categorizes investors into distinct segments, utilizing factors such as sector-specific investment frequencies, investment size, diversification, and historical performance. Machine learning models, such as clustering algorithms or neural networks, analyze the multidimensional nature of this data to recognize commonalities among investors and allocate them into specific groups or segments. Additionally, the system might employ regression analysis or predictive modeling to forecast potential future investment inclinations based on past behavior. The selection process involves prioritizing and determining a predetermined first set of investors based on these identified segments, thereby highlighting those who have consistently shown a historical inclination towards investing in healthcare equity. This approach enables a highly technical and data-driven methodology to accurately identify and rank investors who are more likely to support diverse and underserved communities achieve healthcare equality.

Clearly and effectively communicating the results of the financial model to investors is a necessary driver for obtaining financial investments. First Transmittal Module 800 transmits potential future earnings and other return on investment indicators to a predetermined first set of investors 801 to facilitate a first financial investment in clinical treatments that target inequity-disease causing factors for the equity-affected diseases. The predetermined first set of investors 801 include those investors that have previously invested in a meaningful way in healthcare services targeting diverse and underserved communities. These services may include therapeutics, drugs, clinical studies, diagnostic services, mental health services, behavior health services and community health and wellness programs to name a few. The results of the financial model can include data-driven presentations, financial projections, return on investment metrics, risk assessment, market opportunity, efficiencies and cost reductions, case studies and success stories, and impact investor statements. The results of the future earning and other return on investment indicators can be communicated to investors using any number of vehicles such as data rooms, investor portals, mobile applications, emails, videoconferences, secure file sharing, online reporting tools, online portals for social responsibility reporting, dedicated communication platforms, secure messaging apps, physical reports and meetings etc.

Monitoring the reduction in the prevalence of equity-affected diseases after financial investment is a complex and dynamic process. The equity evaluation processor 1000 continuously monitors the change in the prevalence of equity-affected diseases after the first financial investment. It may include data integration, real-time feeds, geospatial analysis to track disease prevalence in targeted diverse and underserved communities, dashboard reporting, alerts and notifications. Other measures can include electric health records, patient surveys and feedback, clinical quality metrics, health disparity metrics, health impact assessments, and government and public health agency benchmarking. A monitoring processor 1016 utilizes advanced algorithms and data sources to assess the impact of the targeted healthcare initiatives and interventions on health equity for diverse and underserved communities.

Assessing the effectiveness of investments in healthcare for diverse and underserved communities is a multifaceted process that involves evaluating various factors related to healthcare outcomes, equity, and community well-being. Equity Evaluation processor 1000 not only predicts but actively evaluates the potential impact of financial investments in clinical treatments that target inequity-disease causing factors. Evaluation processor 1000 may include key health indicators, such as mortality rates 1001, disease prevalence 1002, and quality of life 1003 in minority communities to assess whether these outcomes are improving or remaining stable. Quality of healthcare provided to diverse and underserved communities may also include evaluating the access to timely and appropriate care, adherence to clinical guidelines, changes in health knowledge and health-seeking behaviors, and patient satisfaction. It is common to use a combination of qualitative and quantitative methods to gain a comprehensive understanding of whether these investments are achieving their intended goals and improving the health and well-being of diverse and underserved communities.

A health segmentation data profiler processor 1026 is configured to identify a health equity funding pool comprised of one or more investors that have not previously invested in health equity but who have shown an unrevealed predisposition to invest in healthcare treatments to benefit diverse and underserved groups. Configuring a health segmentation data profiler processor to identify a health equity funding pool comprising investors who haven't previously invested in health equity but demonstrate a predisposition to support healthcare treatments for diverse and underserved groups is paramount. The health segmentation data profiler processor 1026 can uncover potential investors who might not overtly appear as suitable candidates for health equity investments, especially to the untrained eye. It does so by examining a diverse range of behavioral, financial, and social indicators that, when assessed collectively, reveal a predisposition towards supporting healthcare treatments for underserved groups. This includes not just financial data but also philanthropic activities, social impact statements, partnerships with organizations addressing social determinants of health, social media posts or involvement in community programs. For instance, an investor might support initiatives aimed at education, housing, or employment opportunities in marginalized areas without directly associating these efforts with health equity. However, a data profiler equipped with sophisticated algorithms can identify nuanced factors and correlate indirect contributions and the potential alignment with health equity goals. This unconventional approach distinguishes investors whose interests and actions, although not explicitly within the health equity domain, are likely to engage in supporting diverse and underserved communities' healthcare needs. The profiler's ability to decipher these complex, multi-dimensional indicators is crucial in identifying investors who might not fit the typical mold but harbor genuine potential for fostering health equity through their investments. This targeted approach serves as a crucial step towards addressing health disparities. A second transmittal module 1020 transmits potential future earnings for equity-affected diseases that did not decrease after the first financial investment to a health equity investor funding pool 1100 to further increase the potential for investment in equity-affected diseases.

At least the data mining processor 100, the disease data processor 200, the equity-affected disease identification processor 300, the clinical decisions processing system 400, the ethical artificial intelligence assessment processor 500, the financial forecasting processor 700, the investor segmentation and profiling processor 727, and the health segmentation data profiler processor 1026 each being a separate processor located in a separate housing for security and ease of disaster recovery. The segregation of processors, while not conventional or apparent, assumes a critical role in maintaining security. By compartmentalizing specific processors in distinct housing and dedicated to distinct tasks, the confidentiality and integrity of sensitive information remain intact. This separation not only ensures a targeted focus on privacy but also bolsters the strength of security protocols. Through this segregation, the likelihood of unauthorized access or inadvertent exposure of sensitive data is significantly reduced. Placing processors in separate housing, also known as physical or logical isolation, significantly enhances security in several ways. Housing processors separately ensures that each unit operates independently. If one processor is compromised due to a security breach or malfunction, the others remain unaffected, preventing the spread of potential threats across the system. By segregating processors, the attack surface, or the potential entry points for attackers, is reduced. This isolation limits the pathways that cyber threats can use to infiltrate or disrupt the system. Individual housing allows for better containment of any security incident. If a breach occurs in one processor, the impact is confined to that particular unit, facilitating prompt detection, containment, and resolution. Separating processors aids in safeguarding sensitive data and maintaining the integrity of information. It helps in protecting personally identifiable information and critical data, as the access to and interaction with this data can be more controlled and monitored. If one processor fails or faces an issue, having separate housing ensures redundancy. The unaffected processors can continue to function, providing continuity of services and preventing disruptions in critical operations. For organizations operating in industries with strict regulatory requirements, such as the healthcare industry, segregating processors can assist in meeting compliance standards, as it demonstrates a commitment to data security and privacy. The use of separate housing for processors also plays a pivotal role in fortifying disaster recovery measures within a system. Should an unforeseen catastrophe or system failure occur, the isolation of processors significantly enhances the recovery process. By housing processors separately, the impact of a disaster or failure on one processor is contained, preventing widespread disruption to the entire system. This containment allows for focused remediation efforts on the affected processor, facilitating faster recovery and minimizing downtime. Moreover, the segregated housing design ensures that in the event of damage or malfunction in one area, the other processors remain unaffected and operational. This redundancy is a critical aspect of disaster recovery, as it enables seamless continuation of essential operations and services, safeguarding against extensive data loss and aiding in the swift restoration of normal functionalities. Ultimately, separate housing serves as a fundamental element in enhancing the resilience and expedience of disaster recovery protocols.

The first transmittal module and second transmittal module are each equipped with a dedicated processor for filtering and purging personally identifiable information while retaining sufficient information to encryptically transmit potential future earnings and returns-on-investments for clinical treatments for inequity-disease causing factors for equity-affected diseases. Personally identifiable information can be effectively removed through several methods to safeguard individual privacy and data security. Anonymization stands as a suitable approach, involving the elimination or alteration of direct identifiers such as names, social security numbers, or precise addresses, rendering data anonymous. Pseudonymization can replace direct identifiers with artificial identifiers, allowing diversity and data pertaining to underserved groups data to be matched without revealing personal details. Another method involves data aggregation, where individual data is grouped or summarized to prevent identification. Redaction selectively omits or masks specific PII elements from documents or records, ensuring sensitive information is concealed. These methods, either used alone or in combination, serve to effectively strip PII, safeguarding sensitive information while enabling legitimate and secure data identifying inequity-disease causing factors for the equity-affected diseases to be transmitted securely. Importantly, however, the dedicated processors within each transmittal module are programmed to retain pertinent diversity, race, gender, income, socio-economic and data indicative of underserved groups. These retained data points are encrypted and then securely transmitted, ensuring that the transmission process is both secure and devoid of personally identifiable information. Encryption encodes data, requiring a decryption key to access personal details. Data can be encrypted for transmission using cryptographic techniques that encode information, rendering it unreadable without the appropriate decryption key. This process can involve converting plaintext data into ciphertext through algorithms, making it indecipherable to unauthorized parties. The encrypted data, often using strong encryption is transmitted securely over networks. The recipient possessing the decryption key can then decode the ciphertext back into its original, readable format, ensuring the confidentiality and integrity of the transmitted information. The encrypted transmission of potential future earnings and returns-on-investments for clinical treatments for inequity-disease causing factors for equity-affected diseases, stripped of personal identifiers, facilitates comprehensive artificial intelligence data analysis to address and combat diseases disproportionately affecting diverse and underserved populations, thus contributing to improved healthcare interventions and equity in disease management.

Figure 2:
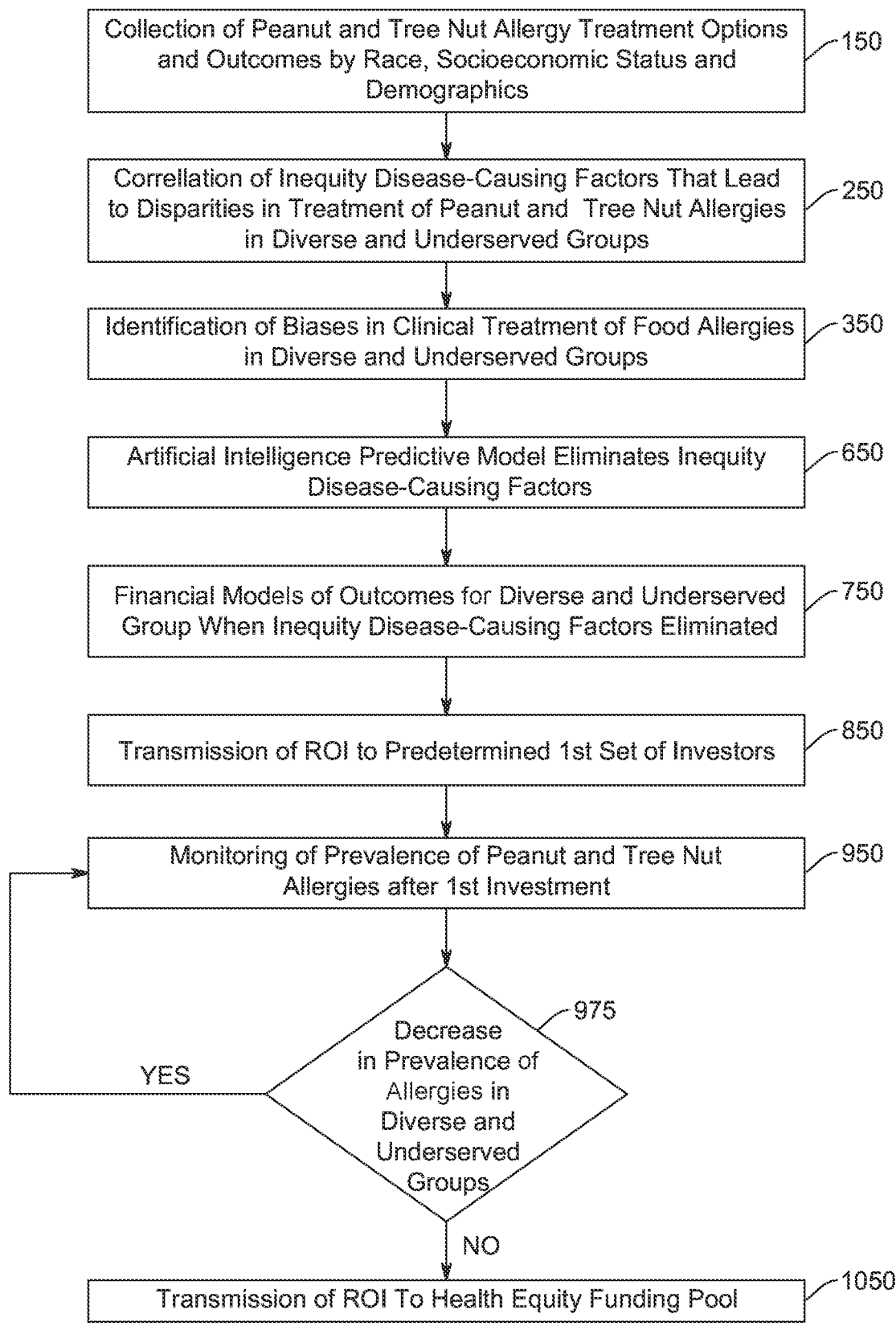
FIG. 2 is a flow diagram of an exemplary embodiment of the present invention for peanut and tree nut food allergies.

FIG. 2 is a flow diagram of a representative example of the present invention to address health inequalities in diverse and underserved groups suffering from food allergies, particularly peanut and tree nut allergies. In step 150, data mining processor 100 obtains information from various clinical trials (Phases I-IV) of approved food allergy therapies, including, for example, drugs such as Palforzia® (peanuts), and post-approval patient treatment monitoring. This step takes into account race, socioeconomic status and demographic information from the clinical trial participants, treatment option users, and those with peanut and tree nut allergies that did not partake in any treatment for their allergies. Peanut and tree nut allergies, like many allergies, often affect diverse and underserved groups disproportionately because of a number of inequity disease-causing factors including genetic and environmental factors. For example, genetic predisposition is an inequity disease-causing factor that can influence an individual's susceptibility to food allergies. Living in or around a so-called food desert is an inequity disease-causing factor that disproportionately affects diverse and underserved groups. Food deserts negatively affect diverse and underserved groups by limiting access to healthy and allergen-free foods. In the absence of readily available allergen-free, nutritious foods, individuals in food deserts are more likely to rely on convenience stores, fast-food restaurants, and other outlets that offer primarily processed and often allergy containing foods that may not be properly labeled with allergens such as peanuts and tree nuts. Lack of a varied diet and exposure to various processed and/or allergy containing foods can influence the development of food allergies. Different dietary patterns can affect the gut microbiome, which is thought to play a role in allergy development. Health disparity is another inequity disease-causing factor because chronic diseases and other health issues often compound the adverse effects of a peanut or tree nut allergy. Economic challenges are another inequity disease-causing factor which not only limits treatment options but also travel to locations that offer novel treatment, immunotherapies and clinical food challenge options. This can be economically burdensome, especially for low-income individuals who may not have reliable transportation. Limited access to allergen-free food and treatments are inequity disease-causing factors that contribute to stress and anxiety for individuals and families who suffer from peanut and tree nut allergies. Reduced opportunities for allergy education is another prevalent inequity disease-causing factor. Those that have limited exposure to food allergy education and resources often cannot make informed decisions concerning food safety and available treatments, thereby perpetuating their food allergy disability. Likewise, socioeconomic status can influence an individual's ability to access healthcare services, purchase allergen-free foods, and receive education about food allergies.

Step 150 further collects information on health outcomes for those suffering from peanut and tree nut allergies, including, for example: symptom scores, reduction in allergy symptoms and incidence of anaphylaxis (a known cause of death for those suffering from food allergies); quality of life metrices indicative of the impact of allergy treatment on a patient's overall quality of life, including physical and mental well-being; use of allergy symptom reduction medications (e.g., antihistamines, decongestants, corticosteroids); allergen-specific immunological levels from skin prick tests or serum biomarkers which measure allergen-specific IgE and IgG antibody levels to assess the body's immune response to allergens; clinical endpoints for severe allergies, such as incidence of anaphylaxis events, other allergic reactions (rashes, abdominal distress etc.), emergency department visits and hospitalizations; patient-reported outcomes to capture the patient's perspective on the impact of treatment on their allergies, including treatment satisfaction and treatment-related adverse events; duration effect to assess how long the treatment's effects last; adverse events or side effects related to the treatment, as these can influence the risk-benefit profile; and cost-effectiveness of the treatment by considering factors like healthcare utilization, productivity, and quality-adjusted life years.

Step 150 also tracks peanut and tree nut allergy severity as individuals with peanut allergies and tree nut allergies may experience a wide range of symptoms when exposed to peanuts or tree nuts. For example, mild allergic reaction symptoms are usually limited to mild skin or gastrointestinal reactions, such as hives, redness, itching, stomach cramps, or mild nausea. Mild reactions are uncomfortable but not life-threatening. Antihistamines may help alleviate these symptoms. Moderate allergic reactions involve more pronounced symptoms that affect multiple organ systems. These may include more severe hives, swelling of the face, lips, or tongue (angioedema), and gastrointestinal symptoms like vomiting or diarrhea. These reactions can be concerning and may require medical attention, typically in the form of antihistamines and possibly epinephrine. Severe allergic reactions (Anaphylaxis) are the most severe and life-threatening form of peanut or tree nut allergies. Symptoms can include difficulty breathing, a drop in blood pressure, loss of consciousness, severe swelling, severe hives, and gastrointestinal distress. Anaphylaxis requires immediate treatment with epinephrine, an injection that can reverse the allergic reaction. Without prompt intervention, anaphylaxis can be fatal.

Step 250 correlates the aforementioned health outcomes to inequity disease-causing factors that lead to disparities in outcome for diverse and underserved groups. By correlating the inequity disease-causing factors with negative outcomes, biases and inequities in the treatment of peanut and tree nut allergies are identified. By examining the complex interplay between various factors, such as disparities in peanut and allergy treatments, food deserts, health inequities, genetic predisposition, socioeconomic disparities, geographical influences, and healthcare access, valuable insights into the root causes of inequitable health outcomes among diverse and underserved populations suffering from food allergies is obtained. Step 350 then identifies the biases in clinical treatment of food allergies in diverse and underserved groups to then correct them in the following step. For example, ethical artificial intelligence assessment processor 500 can identify biases in clinical treatment of food allergies in diverse and underserved groups using advanced machine learning and data analysis techniques, as described in detail above in connection with FIG. 1.

Step 650 leverages artificial intelligence and EADAA 601 to refine existing clinical outcomes associated with peanut and tree nut allergies in diverse and underserved groups. This innovative approach seeks to rectify biases and account for factors contributing to inequities in peanut and tree nut outcome predictions in diverse and underserved groups. For example, the equity-affected disease adjustor processor 600 of FIG. 1 can adjust clinical outcomes of the equity-affected diseases when correcting the biases and the inequity disease-causing factors. By employing advanced statistical and machine learning techniques and fairness-aware algorithms, biases are systematically removed thereby allowing the novel system to predict equitable health outcomes and the financial benefit to investors of such outcomes. It is well-acknowledged that biases in healthcare data and underrepresentation of diverse and underserved groups result in misdiagnoses or suboptimal treatment recommendations for those groups, including for those diverse and underserved patients suffering from peanut and tree nut disabilities. With the correction of these biases, the predictive model of this invention described herein offers more precise and tailored insights as to the financial benefits of addressing peanut and tree nut allergy disabilities in diverse and underserved communities. Additionally, this comprehensive approach ensures that resources in healthcare are allocated more judiciously amongst those diverse and underserved individuals suffering from food allergy disabilities.

Step 750 adapts the artificial intelligence tailored predictions and provides a financial model of the financial benefits of treating peanut and tree nut allergy disabilities in diverse and underserved patients taking into account clinical biases and factors contributing to health disparities. For example, the financial forecasting processor 700 of FIG. 1 uses artificial intelligence to calculate potential future earnings and return-on-investment of clinical treatments of equity-affected diseases. The versatile platform of FIG. 2 is tailor-made for estimating future earnings for those investing in the treatment of peanut and tree nut allergies among diverse and underserved groups. Step 750 harmonizes peanut and tree nut healthcare data from various sources to forecast earnings based on anticipated treatment outcomes, all while integrating corrections to mitigate biases and inequity disease causing factors. Crucially, the system employs fairness metrics to assess the accuracy and equitability of these projections across diverse and underserved patients. The financial models generated by Step 750 serve as a compelling prompt for investors, highlighting the financial incentives of addressing peanut and tree nut allergies in diverse and underserved communities. These models encompass a comprehensive analysis, including market size, growth potential, patient volume, reimbursement rates, tax incentives, and the costs linked to investment in healthcare tailored to these populations. By presenting multiple scenarios and expected returns on investment derived from tailoring services and clinical treatments for these communities, investors gain insight into the data-driven rationale for supporting food allergy solutions for diverse and underserved populations, thereby fostering not only financial rewards but also advancing health equity.

Step 850 transmits to a predetermined first set of investors the return-on-investment metrics and future earning for treatment of peanut and tree nut allergies in diverse and underserved patients once the inequity disease-causing factors have been eliminated. For example, first transmittal module 800 of FIG. 1 can be used to transmit this information to a first set of predetermined investors. Effectively conveying the outcomes of the financial model to investors is a crucial catalyst for securing financial support. Step 850 serves as the conduit for transmitting potential future earnings and other key return-on-investment metrics to a predefined initial group of investors. This outreach aims to attract initial financial investments dedicated to clinical treatments that specifically target the root causes of food allergy inequities in diverse and underserved patients. The outcomes of this financial model encompass data-driven presentations, financial forecasts, return-on-investment assessments, risk evaluations, market opportunities, operational efficiencies, cost reductions, illustrative case studies, success narratives, and impact-driven investor statements all directed to peanut and tree nut treatments in diverse and underserved patients. These future earnings and return-on-investment for food allergies, and in particular peanut and tree nut allergies, can be communicated to investors via a diverse array of mediums, including data rooms, investor portals, mobile applications, emails, videoconferencing, secure file sharing, online reporting tools, platforms dedicated to social responsibility reporting, specialized communication platforms, secure messaging applications, physical reports, and in-person meetings, facilitating comprehensive engagement and understanding.

Step 950 monitors the reduction in the prevalence of peanut and tree nut allergy disabilities following an initial financial investment in accordance with the present invention. A monitoring processor, such as monitoring processor 1016 of FIG. 1, designed for continuous tracking of changes in the prevalence of such disabilities post the first financial investment can encompass various components, including data integration, real-time data updates, geospatial analysis for monitoring disease prevalence within diverse and underserved communities, dashboard reporting, and alerts. Additional measures involve the utilization of electronic health records, patient surveys, feedback mechanisms, clinical quality metrics, health disparity metrics, health impact assessments, and benchmarking against government and public health agency standards. The monitoring process evaluates the impact of targeted healthcare initiatives and interventions on peanut and tree nut allergy equity within diverse and underserved communities to determine the impact of the first investment.

Step 975 evaluates the effectiveness of healthcare investments for peanut and tree nut allergies in diverse and underserved communities in a multifaceted undertaking that encompasses the assessment of various factors related to healthcare outcomes, equity, and community well-being. For example, evaluation processor 100 of FIG. 1 determines clinical effects of the first financial investment. Step 975 ascertains the impact of financial investments in peanut and tree nut allergy clinical treatments in diverse and underserved patients in accordance with the undertakings of the current invention. This evaluation may consider essential health metrics, such as mortality rates, disease allergy prevalence, allergy reaction occurrence and duration, and life expectancy within minority communities, to gauge whether these indicators are showing improvement or stability. If the health metrics for peanut and tree nut in diverse and underserved communities improve after the first investment, then monitoring step 950 continues. If the health metrics for peanut and tree nut allergies in diverse and underserved communities does not improve then the system moves to Step 1050.

Step 1050 conveys to a health equity investor funding pool potential future earnings associated with peanut and tree nut allergy disabilities that persisted following the initial financial investment with the aim of further bolstering investments in food allergy treatments in diverse and underserved patients. For example, second transmittal module 1020 can transmit to a second set of potential investors in a health equity funding pool the potential future earnings and return-on-investment associated with addressing peanut and tree nut disabilities in diverse and underserved patients. This group of prospective investors encompasses entities that previously had no healthcare investments in food allergy treatment for diverse and underserved communities but have been identified as likely candidates for such investments based on their related financial commitments. Identifying institutions inclined to invest in food allergy health equity for diverse and underserved communities entails scrutinizing particular traits and indicators that signal a dedication to addressing healthcare disparities and advancing equitable health outcomes. The second transmittal model can pinpoint such potential investors by examining mission and values statements, with a focus on language emphasizing diversity, inclusion, and a commitment to mitigating health disparities. It also evaluates an institution's diversity in leadership, its initiatives centered on equity, community partnerships, as well as any accolades or acknowledgments related to their efforts in promoting diversity and social equity.

Figure 3:
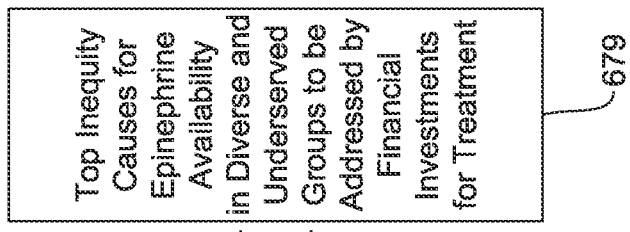
FIG. 3 is a diagrammatic overview of an exemplary embodiment for addressing equitable distribution of epinephrine auto-injectors in accordance with the present invention.

FIG. 3 is a system overview of an exemplary embodiment for financial investment in epinephrine auto-injector distribution in diverse and underserved patients in accordance with the present invention. Epinephrine auto-injectors are medical devices containing adrenaline, utilized to address severe allergic reactions, specifically anaphylaxis, a life-threatening condition triggered by allergens like peanut and tree nut containing foods. This auto-injector device, sold under brand names such as EpiPen® and Auvi-Q®, is skillfully designed for swift and straightforward epinephrine administration during emergency situations. It operates as a one-time-use auto-injector, automatically delivering a precise epinephrine dose upon contact with the skin, typically the thigh. Epinephrine counteracts the severe symptoms of anaphylaxis, including breathing difficulties, facial and throat swelling, plummeting blood pressure, and other critical manifestations. Epinephrine medical auto-injectors are frequently prescribed to individuals with known peanut and tree nut allergies who are at risk of anaphylactic episodes.

Unfortunately, epinephrine auto-injector availability among diverse and underserved groups lags significantly as compared to among affluent or well-served groups. The present invention can be better coordinate, focus and facilitate the application of financial investment in healthcare programs to provide equitable and just availability of epinephrine auto-injectors among diverse and underserved groups. As shown in FIG. 3, epinephrine auto-injector availability is first determined from various health records in module 675. For example, pharmacies maintain records of epinephrine auto-injector prescriptions and purchases. Insurance companies collect data on the medications and medical devices that are prescribed and reimbursed including for epinephrine auto-injector prescriptions. Pharmaceutical companies often conduct clinical trials and studies to assess the usage and effectiveness of epinephrine auto-injectors. These studies generate data on how epinephrine auto-injectors are distributed and used in controlled settings. Emergency Medical Services (EMS) data is sourced from EMS providers and hospitals which collect data on the administration of epinephrine during emergency situations, such as anaphylactic reactions. Researchers often use patient surveys and questionnaires to collect data on epinephrine auto-injector availability among individuals with allergies. Pharmaceutical sales data can show how many epinephrine auto-injectors are sold in a given region or timeframe. This data may not directly reflect usage but can provide insights into demand. Electronic health records (EHR) and medical records maintained by healthcare providers will contain information about epinephrine auto-injector prescriptions and their use in clinical settings. National and regional public health agencies may compile data on anaphylactic reactions and the availability of epinephrine auto-injectors. Adverse event reporting systems show adverse events related to epinephrine auto-injector usage, and therefore epinephrine auto-injector availability. It's important to note that accessing and using this data may require proper permissions, privacy considerations, and adherence to regulations, especially when dealing with patient-specific information. Researchers, healthcare providers, and pharmaceutical companies often collaborate to gather and analyze data on epinephrine auto-injector usage to better understand its effectiveness and improve patient outcomes.

Race information in module 676, income level information in module 677, and epinephrine auto-injector availability factors in module 678 are extracted from the sources of module 675. The availability of epinephrine auto-injectors to diverse and underserved communities can be influenced by a variety of factors. The presence and quality of healthcare facilities, clinics, and pharmacies in a community play a crucial role in epinephrine auto-injector availability. Underserved areas with limited access to healthcare services may struggle to provide epinephrine auto-injector to residents. The extent of health insurance coverage can affect access to epinephrine auto-injector. Communities with higher rates of uninsured or underinsured individuals may face barriers to obtaining epinephrine auto-injector due to cost. Economic factors, including income levels and employment opportunities, can impact access to epinephrine auto-injectors. Lower-income communities may have a harder time affording epinephrine auto-injector, even with insurance. Rural areas may have limited access to healthcare resources, including pharmacies. The distance to the nearest healthcare provider or pharmacy can affect epinephrine auto-injector availability. Language barriers and cultural factors can impact access to healthcare and medication. Communities with diverse populations may need tailored outreach and education efforts to ensure people understand the importance of epinephrine auto-injectors. The level of education and awareness within a community can influence epinephrine auto-injector usage. Effective public health campaigns and education programs can increase awareness of anaphylaxis and the need for epinephrine auto-injectors. Local, state, and national regulations can affect the availability of epinephrine auto-injectors. Regulatory changes, pricing, and access policies can have a significant impact. Socioeconomic disparities, including disparities in access to transportation and technology, can affect one's ability to obtain epinephrine auto-injectors. Access to online resources for prescription ordering and health information is often unequally distributed. Issues within the supply chain, including manufacturing and distribution delays, can lead to shortages and affect availability in certain regions. The requirement for a prescription to obtain epinephrine auto-injectors may hinder access in some areas, particularly if individuals have limited access to healthcare providers. Collaborations between healthcare providers, local organizations, and pharmaceutical companies can improve epinephrine auto-injector availability through programs that offer discounts, subsidies, or free epinephrine auto-injector to underserved communities. The availability and response time of emergency medical services can also influence access to epinephrine auto-injectors, as timely administration is critical during anaphylactic emergencies.

Module 679 provides the top inequity causes for epinephrine auto-injector availability in diverse and underserved groups. By identifying these causes, target financial modeling of investments for addressing these causes, and therefore providing equitable availability of epinephrine auto-injectors, can be achieved. Using artificial intelligence employing statistical and machine learning techniques and fairness-aware algorithms, the present invention provides precise cases that would most benefit from financial investment for diverse and underserved groups lacking epinephrine auto-injector availability. Understanding the root causes of the scarcity of epinephrine auto-injectors in diverse and underserved communities is a crucial step in catalyzing financial investment to rectify this issue. Identifying these causes, whether they be related to healthcare disparities, economic barriers, or logistical challenges, enables investors to develop targeted solutions that address the specific needs of these communities. With this knowledge, investors can recognize the potential for substantial financial returns while simultaneously championing improved health equity. By better coordinating, focusing and facilitating initiatives that alleviate these barriers and increase epinephrine auto-injector availability, not only do investors stand to benefit financially, but they also contribute to a more inclusive and accessible healthcare landscape for underserved and diverse populations, ultimately fostering a healthier and more equitable society.

Figure 4:
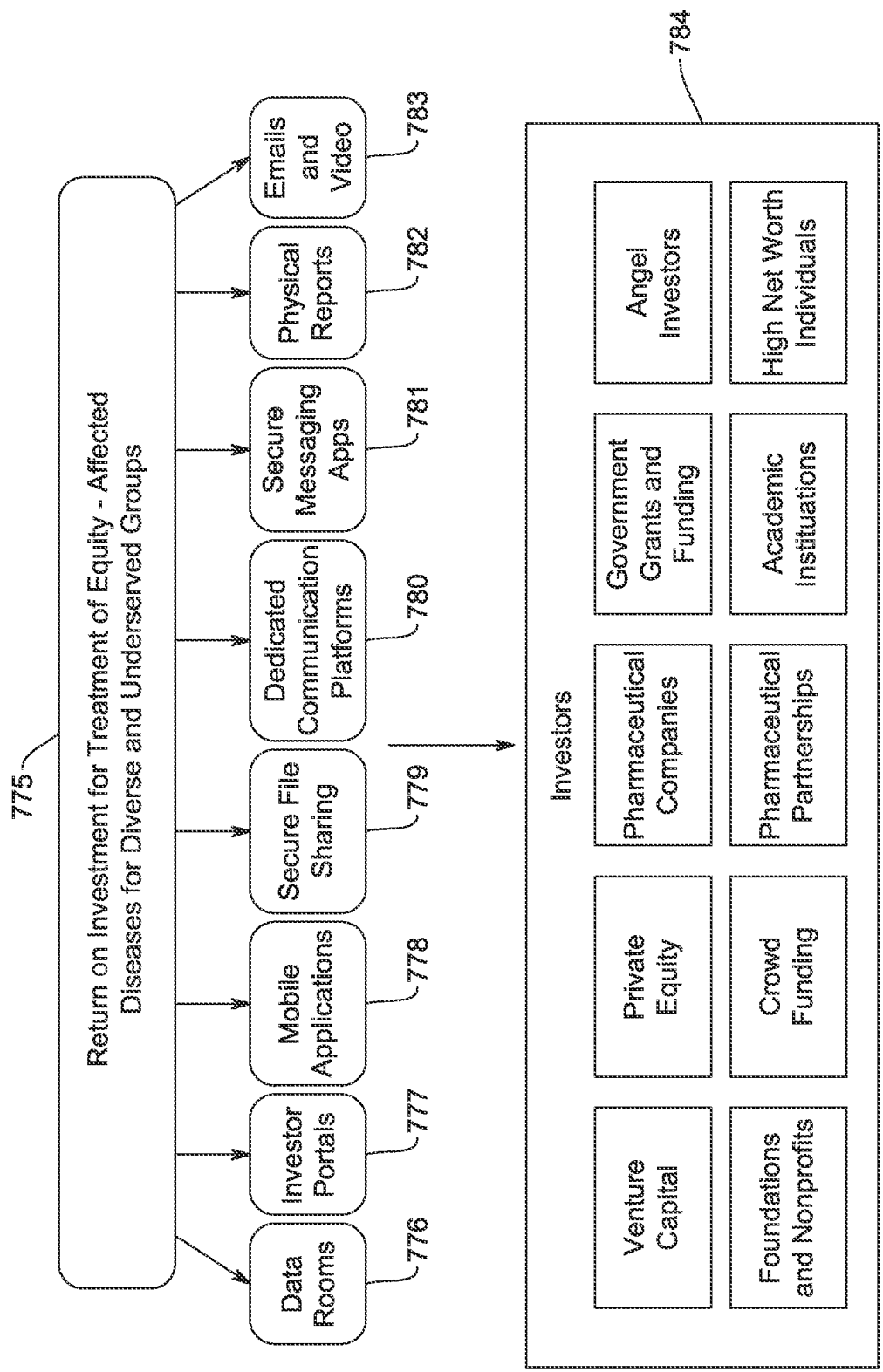
FIG. 4 is a diagrammatic overview of an exemplary embodiment to facilitate financial investment for the treatment of equity-affected diseases in accordance with the present invention.

FIG. 4 is an overview of an exemplary embodiment of the transmission of the return of investment for the treatment of equity-affected diseases for diverse and underserved groups after removal of the inequity disease-causing factors. This financial information 775 may be transmitted through one or more secure vehicles for the transmission of data including, data rooms 776, investor portals 777, mobile applications 778, secure file sharing 779, dedicated communication platforms 780, secure messaging apps 781, physical reports 782, emails/video 783 etc. Investors 784 for treatment of equity-affected diseases in diverse and unserved groups are wide-ranging and multifaceted. Venture capital firms invest in biotechnology and pharmaceutical startups that are developing new drugs, therapies, or medical technologies. These investments are typically in exchange for equity in the company. Private equity firms may invest in more established pharmaceutical companies or those in later stages of drug development. They provide capital in exchange for equity or ownership stakes in the companies. Large pharmaceutical companies often fund their own research and development efforts. They may also collaborate with or acquire smaller biotech firms working on promising drug candidates. Government agencies, such as the National Institutes of Health (NIH) in the United States, provide grants and funding opportunities for academic researchers and biotech companies involved in drug development and clinical trials. Individual angel investors with an interest in the healthcare and biotechnology sectors may provide funding to startups and early-stage drug development projects. Some foundations and nonprofit organizations offer funding for research and clinical trials in specific disease areas. In recent years, crowdfunding platforms have been used to raise funds for specific drug development projects and clinical trials, often by connecting with patients and advocacy groups. Collaborative agreements between pharmaceutical companies, academic institutions, and smaller biotech firms can provide funding for drug development and clinical trials. These partnerships may include licensing agreements and milestone payments. Organizations dedicated to specific diseases or conditions, such as the American Cancer Society or the Cystic Fibrosis Foundation, may offer research grants and funding opportunities. Universities and research institutions may allocate funds for drug development and clinical trials through internal grants and research budgets. Some biotech companies raise funds by going public (IPO), allowing them to generate capital by selling shares to the public. Collaboration with healthcare and biotech companies, contract research organizations (CROs), and clinical research organizations (CROs) can provide financial and logistical support for clinical trials. Some patient advocacy organizations and rare disease groups play a role in funding and supporting research and clinical trials in their areas of interest. High net worth individuals, often with a background or interest in the life sciences, may invest in drug development projects and clinical trials. The availability and suitability of funding therapies and treatments that disproportionately affect diverse and underserved groups may vary depending on the level of commitment needed, the specific therapeutic area, and geographic location. In many cases, a combination of these funding sources is used to support an enterprise approach to achieving healthcare equity.

Figure 5:
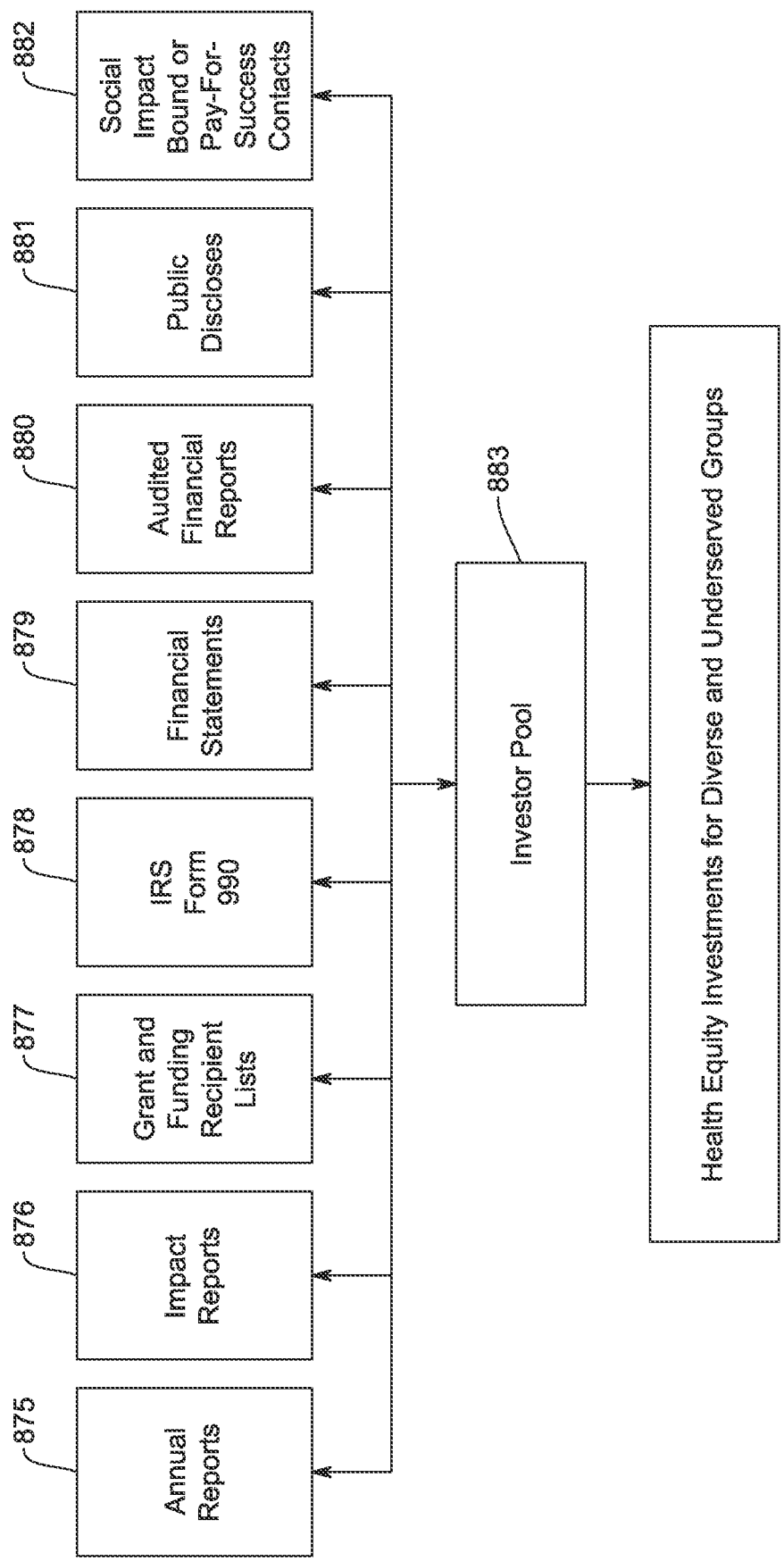
FIG. 5 is a diagrammatic overview of an exemplary embodiment of the facilitation of the application of financial investments to an investor pool for health equity investments in accordance with the present invention.

FIG. 5 is an overview of an exemplary embodiment of the selection process for determining those investors that are most likely to provide a financial investment to treating equity-affected diseases for diverse and underserved groups. Artificial intelligence trained on reading financial data holds the potential to be a powerful tool in uncovering potential investors for therapies aimed at diverse and underserved groups. By analyzing financial information, AI can identify investors or investment firms that have a history of supporting healthcare projects, particularly those focused on diverse and underserved populations. This finance information includes annual reports 875, impact reports 876, grand and funding recipient lists 877, IRS Form 990 878, financial statements 879, audited financial reports 880, public disclosures 881, partnership agreements, tax filings and regulatory documents and social impact bonds or pay-for-success contracts 882. Annual reports often include sections on corporate social responsibility (CSR) and sustainability initiatives. Mentions of investments or programs related to health equity and community health are key points that the AI trained model will identify. Some organizations, particularly those involved in impact investing or philanthropy, produce impact reports that detail their investments in projects related to health equity. If the organization is a grant-making foundation or supports health equity initiatives, their financial documents may include lists of grant recipients, which can provide insights into their investments in specific health equity projects. U.S. nonprofit organizations are required to file IRS Form 990, which includes information about their finances, governance, mission and program expenses and grants that support health equity. Financial statements, including income statements and balance sheets, identify allocations of funds or expenses related to health equity programs or initiatives. Audited financial reports can offer a more detailed and transparent view of an organization's financial activities, including funds allocated to health equity efforts. An organization's budget or financial plan may include line items related to health equity programs or projects. An organization's website and public disclosures also provide information related to their investments in health equity. If an organization collaborates with other entities on health equity initiatives, the terms and agreements in partnership documents may contain financial information related to the investments. In addition to IRS Form 990, other regulatory documents and tax filings specific to the organization's country have reporting for nonprofit or charitable organizations. If an organization participates in social impact bonds or pay-for-success contracts, the associated financial documents will reveal their investments in health equity initiatives. The AI system of the present invention will discern patterns and preferences, recognizing investors 883 who prioritize healthcare equity and initiatives designed to address the unique needs of diverse communities. In this way, AI can streamline the investor identification process, connecting organizations developing therapies for underserved groups with like-minded financial backers, ultimately advancing the goal of improving healthcare access and outcomes for those who need it most.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

I claim:

1. A system for promoting health equity in diverse and underserved groups, the system comprising:
    a data mining processor for scanning clinical trials, drug applications, government health data, medical research papers, clinical notes, patient records, clinical guidelines, and electronic health records trained using tracking patterns, outlier detection, clustering, regression, and sentiment analysis to collect (i) disease data and (ii) clinical treatment options for said disease data;
    a disease data processor for receiving said disease data from the data mining processor, storing said disease data in a disease database, and correlating said disease data with said clinical treatment options based on race, income, and socio-economic factors;
    an equity-affected disease identification processor configured to systematically scan the disease database for relevant disease data, analyze the clinical treatment options and compare treatment disparities among different demographic groups to categorize diseases based on a magnitude of these disparities to identify one or more equity-affected diseases from said disease database where diverse and underserved groups are disproportionately disadvantaged in said clinical treatment options compared to the general population;
    wherein the equity-affected disease identification processor includes data visualization tools to represent the identified one or more equity-affected diseases, allowing for easier and faster interpretation and decision-making;

a clinical decisions processing system comprising artificial intelligence which receives the relevant disease data from the equity-affected disease identification processor to identify one or more inequity disease-causing factors causing said diverse and underserved groups to suffer disproportionate clinical outcomes for said equity-affected diseases;

an ethical artificial intelligence assessment processor trained on datasets from a wide range of demographic groups to identify one or more biases in the clinical treatment of such equity-affected diseases to determine disparities caused by said biases;

wherein the ethical artificial assessment processor is configured to:

perform preprocessing techniques of data anonymization and de-identification to remove any personally identifiable information to improve the accuracy of the system by reducing the likelihood of perpetuating biases;

conduct regular algorithmic fairness audits to evaluate the processor's performance across different demographic groups, identify hallucinations that emerge over time from an output of the algorithmic fairness audits, update the training data based on peer-reviewed medical training materials and sources, and retrain the ethical artificial assessment processor with the updated training data to improve the accuracy of the system in identifying biases in the clinical treatment of equity-affected diseases;

an equity-affected disease adjustor processor for adjusting clinical outcomes of said equity-affected diseases when correcting said biases and said inequity disease-causing factors, wherein said equity-affected disease adjustor processor includes artificial intelligence trained on finance, biotechnology, and public health disciplines of science to correct said biases and inequity disease-causing factors;

a financial forecasting processor employing a financial forecasting platform for calculating return-on-investment of clinical treatments based on the adjusted clinical outcomes received from the equity-affected disease adjusted processor;

an investor segmentation and profiling processor for determining a predetermined first set of investors based on clustering algorithms trained on both (a) data from known investments in healthcare targeting diverse and underserved communities, and (b) sentiment data from social media posts, public forums, and private investor correspondence that identifies patterns that suggest a positive, previously unexpressed sentiment toward health equity investments;

a first transmittal module for transmitting said return-on-investment to said predetermined first set of investors to coordinate the application of a first financial investment in clinical treatments that target inequity-disease causing factors for said equity-affected diseases;

a monitoring processor for continuously monitoring the change in the prevalence of equity-affected diseases after said first financial investment;

an evaluation processor for determining clinical effects of said first financial investment in said clinical treatments that target inequity-disease causing factors;

a health segmentation data profiler processor configured to analyzes philanthropic activities, social impact statements, organization partnerships and community programs involvement to improve the accuracy of the processor in identifying a health equity funding pool comprised of one or more investors that have not previously invested in health equity but who have shown a predisposition to invest in healthcare treatments to benefit diverse and underserved groups;

a second transmittal module for transmitting to said health equity funding pool said potential future earnings and return-on-investment for equity-affected diseases that did not decrease after said first financial investment to further increase the potential for investment in equity-affected diseases;

the data mining processor, the disease data processor, the equity-affected disease identification processor, the clinical decisions processing system, the ethical artificial intelligence assessment processor, the financial forecasting processor, the investor segmentation, the profiling processor and the health segmentation data profiler processor each being a separate processor located in a separate housing for security and ease of disaster recovery; and the first transmittal module and second transmittal module each equipped with a dedicated processor for filtering and purging personally identifiable information through pseudonymization that replace direct identifiers of personally identifiable information with artificial identifiers while retaining sufficient information to encryptically transmit inequity-disease causing factors for said equity-affected diseases.

2. The system of claim 1, wherein said equity-affected disease is a peanut allergy disability.

3. The system of claim 1, wherein said equity-affected disease is a tree nut allergy disability.

4. The system of claim 1, wherein said first financial investment is for increasing availability of epinephrine auto-injectors for diverse and underserved groups.

5. The system of claim 1, wherein said first financial investment is for oral immunotherapy treatments for diverse and underserved groups suffering from food allergy disabilities.

6. The system of claim 1, wherein said artificial intelligence includes large language models.

7. A method for promoting health equity in diverse and underserved groups, the method comprising:

scanning clinical trials, drug applications, government health data, medical research papers, clinical notes, patient records, clinical guidelines, and electronic health records trained using tracking patterns, outlier detection, clustering, regression, and sentiment analysis to collect (i) disease data and (ii) clinical treatment options for said disease data;

storing said disease data in a disease database and correlating said disease data with said clinical treatment options based on race, income, and socio-economic factors;

identifying, using data visualization tools to represent the identified disease data, one or more equity-affected diseases from said disease database where diverse and underserved groups are disproportionately disadvantaged in said clinical treatment options compared to the general population;

using artificial intelligence to identify one or more inequity disease-causing factors causing said diverse and underserved groups to suffer disproportionate clinical outcomes for said equity-affected diseases;

training said artificial intelligence on datasets from a wide range of demographic groups wherein said training includes:

performing preprocessing techniques of data anonymization and de-identification to remove any personally identifiable information to improve the accuracy of the system by reducing the likelihood of perpetuating biases;

conducting regular algorithmic fairness audits to evaluate the performance across different demographic groups, identifying hallucinations that emerge over time from an output of the algorithmic fairness audits, updating the training data based on peer-reviewed medical training materials and sources, and re-training the ethical artificial assessment processor with the updated training data to improve the accuracy of the system in identifying biases in the clinical treatment of equity-affected diseases;

identifying one or more biases in the clinical treatment of such equity-affected diseases to determine disparities caused by said biases;

adjusting clinical outcomes of said equity-affected diseases when correcting said biases and said inequity disease-causing factors, using artificial intelligence trained on finance, biotechnology, and public health to correct said biases and inequity disease-causing factors;

calculating return-on-investment of clinical treatments of said equity-affected diseases when accounting for said biases and inequity disease-causing factors;

training artificial intelligence to determining a predetermined first set of investors using clustering algorithms trained on both (a) data from previous known in healthcare targeting diverse and underserved communities, and (b) sentiment data from social media posts, public forums, and private investor correspondence that identifies patterns that suggest a positive, previously unexpressed sentiment toward health equity investments;

transmitting said return-on-investment to said predetermined first set of investors to coordinate the application of a first financial investment in clinical treatments that target inequity-disease causing factors for said equity-affected diseases;

continuously monitoring the change in the prevalence of equity-affected diseases after said first financial investment;

determining clinical effects of said first financial investment in said clinical treatments that target inequity-disease causing factors;

identifying a health equity funding pool comprised of one or more investors that have not previously invested in health equity but who have shown a predisposition to invest in healthcare treatments to benefit diverse and underserved groups;

transmitting to said health equity funding pool said return-on-investment for equity-affected diseases that did not decrease after said first financial investment to further increase the potential for investment in equity-affected diseases;

physically separating for security and ease of disaster recovery the mechanisms for scanning health predominant sources, identifying one or more equity-affected diseases, identifying one or more inequity disease-causing factors, identifying one or more biases in the clinical treatment of such equity-affected diseases, adjusting clinical outcomes of said equity-affected diseases, calculating return-on-investment of clinical treatments of said equity-affected diseases, determining a predetermined first set of investors, transmitting said potential future earnings to said predetermined first set of investors, continuously monitoring the change in the prevalence of equity-affected diseases, determining clinical effects of said first financial investment, and identifying a health equity funding pool; and filtering and purging personally identifiable information while retaining sufficient information to encryptically transmit inequity-disease causing factors for said equity-affected diseases.

8. The method of claim 7, wherein said equity-affected disease is a peanut allergy disability.

9. The method of claim 7, wherein said equity-affected disease is a tree nut allergy disability.

10. The method of claim 7, wherein said first financial investment is for increasing availability of epinephrine auto-injectors for diverse and underserved groups.

11. The method of claim 7, wherein said first financial investment is for oral immunotherapy treatments for diverse and underserved groups suffering from food allergy disabilities.

12. The method of claim 7, wherein said artificial intelligence uses large language models.

* * * * *